United States Patent [19]

Andres et al.

[11] Patent Number: 5,420,308

[45] Date of Patent: May 30, 1995

[54] 2,2-DIFLUOROBENZO (1,3)-DIOXOLE-CARBALDEHYDES AND NEW INTERMEDIATE PRODUCTS

[75] Inventors: Peter Andres, Leichingen; Albrecht Marhold, Leverkusen, both of Germany

[73] Assignee: Bayer Aktiengesellschaft, Leverkusen, Germany

[21] Appl. No.: 207,102

[22] Filed: Mar. 4, 1994

Related U.S. Application Data

[63] Continuation of Ser. No. 952,022, Sep. 28, 1992, abandoned.

[30] Foreign Application Priority Data

Oct. 7, 1991 [DE] Germany ............... 41 33 155.9

[51] Int. Cl.⁶ ............................. C07D 317/46
[52] U.S. Cl. ............................ 549/436; 549/434
[58] Field of Search ........................ 549/434, 436

[56] References Cited

U.S. PATENT DOCUMENTS

| | | |
|---|---|---|
| 4,310,540 | 1/1982 | Lantzsch et al. |
| 4,886,816 | 12/1989 | Franckowiak et al. |
| 5,260,460 | 11/1993 | Andres et al. |
| 5,281,725 | 1/1994 | Andres et al. |

OTHER PUBLICATIONS

Eugene L. Stogryn, *J. Org. Chem.*, 1972, p. 673.
A. H. Blatt, *Organic Syntheses*, collective vol. 2, p. 549, 1946.
I. R. C. Bick, Australian Journal of Chemistry, vol. 22, 1969, pp. 1563–1568.

*Primary Examiner*—Nicky Chan
*Attorney, Agent, or Firm*—William C. Gerstenzang; Sprung Horn Kramer & Woods

[57] ABSTRACT

According to the invention, a new process has been found for the preparation of 2,2-difluoro-benzo[1,3]-dioxole-carbaldehydes of the formula (I)

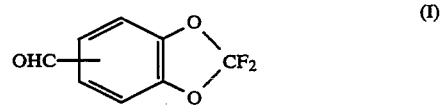

in which benzo[1,3]dioxole-carbaldehydes are chlorinated, the 2,2-dichloro-dichloromethylbenzo[1,3]dioxoles formed, which are likewise new, are partly fluorinated to give the 2,2-difluoro-dichloromethyl-benzo[1,3]dioxoles, which are likewise new, and these are then reacted with urotropin to give the desired compounds.

3 Claims, No Drawings

2,2-DIFLUOROBENZO(1,3)-DIOXOLE-CARBALDEHYDES AND NEW INTERMEDIATE PRODUCTS

This application is a continuation of application Ser. No. 07/952,022, filed Sep. 28, 1992, now abandoned.

The present invention relates to a new process for the preparation of 2,2-difluorobenzo(1,3)dioxole-carbaldehydes, which are used as valuable starting compounds for the synthesis of highly active compounds for combating, for example, pests in plant protection, and new intermediate products.

It is known that 2,2-difluorobenzo(1,3)dioxole-carbaldehydes are obtainable by a procedure in which 4-methylbenzo(1,3)dioxole is used as the starting substance, this is reacted with phosphorus pentachloride and chlorine to give the 2,2-dichloro product, which is then reacted with hydrofluoric acid to give the 2,2-difluoro compound. The methyl group is then brominated and this grouping is finally converted into the aldehyde group with urotropin in a known manner, the desired 2,2-difluoro-benzo(1,3)-dioxole-4-carbaldehyde thus being obtained (compare EP-A 291,779=DE 3,716 652).

Disadvantages of this known process are the four-stage reaction. Furthermore, the poor accessibility and availability of the particular starting materials, coupled with a moderate overall yield of the process.

A synthesis of 2,2-difluoro-benzo(1,3)-dioxole-5-carbaldehyde is moreover known, which uses 5-bromobenzo[1,3]-dioxole as the starting substance, which is chlorinated to give the 2,2-dichloro compound, this subsequently being reacted with hydrofluoric acid in the presence of antimony trifluoride to give the 2,2-difluoro compound, the lithium compound obtained therefrom with butyllithium then being reacted with dimethylformamide to give the desired aldehyde (compare E. L. Storgryn: J. Org. Chem. Volume 37 (1972) No. 4, 673).

This synthesis has not acquired industrial importance. Disadvantages are the use of antimony trifluoride and butyllithium, which firstly are expensive and secondly cause problems during disposal, that is to say the waste products and by-products thereof. Increased safety precautions must also be observed during transportation and handling of butyllithium.

The last step, the reaction of 2,2-difluorobenzo[1,3]-dioxoles with, for example, butyllithium or generally with an alkali metal or a compound of an alkali metal or of an alkaline earth metal with a strong anion base, is described, inter alia, in EP 333,658. The disadvantages are identical to those stated above, and the starting materials used can be obtained, for example, from 1,3-benzodioxole, from which the 2,2-dichloro compound is first prepared (compare DE 3 821 130), and from this the difluoro compound (compare EP 41 131), which is then formylated as described.

The disadvantages have already been listed.

It has now been found that the 2,2-difluoro-benzo[1,3]-dioxole-carbaldehydes of the general formula (I)

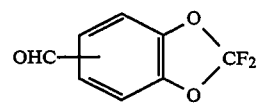

are obtained by reaction of benzo[1,3]dioxole-carbaldehydes of the general formula (II)

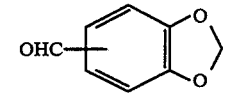

with chlorinating agents, if appropriate in the presence of a solvent, in a 1st stage to give the 2,2-dichloro-dichloromethyl-benzo[1,3]dioxoles of the formula (III)

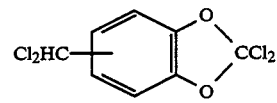

with hydrogen fluoride, if appropriate in the presence of a solvent, in a 2nd stage to give the 2,2-difluoro-dichloromethyl-benzo[1,3]dioxoles of the general formula (IV)

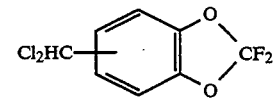

and with urotropin in a known manner in a 3rd stage to give the 2,2-difluoro-benzo[1,3]dioxole-carbaldehydes.

It is to be described as decidedly surprising that the desired products are obtained in a high purity and good yields by the reaction according to the invention. Above all, it is surprising that the partial fluorination of the tetrachloro compound to give the 2,2-difluoro compound in the second stage proceeds so smoothly without any noticeable side reactions. The process according to the invention has a number of advantages over the process which is already known:

Firstly, with a comparable but not identical starting compound, one reaction stage is spared. Secondly, the benzo[1,3]dioxole-carbaldehydes used are also readily accessible in industrial amounts, that is to say there is a better accessibility and availability of the starting materials, and moreover the synthesis gives the desired products in a high purity and good yields.

If, for example, benzo[1,3]-dioxole-4-carbaldehyde and phosphorus pentachloride are used in the 1st stage, hydrofluoric acid is used in the 2nd stage and urotropin is used in a known manner in the 3rd stage, the course of the reaction in the process according to the invention can be represented by the following equation:

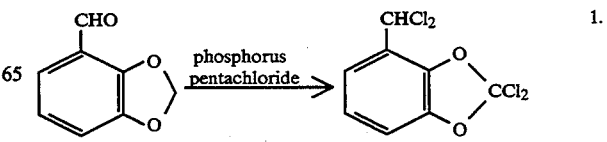

1.

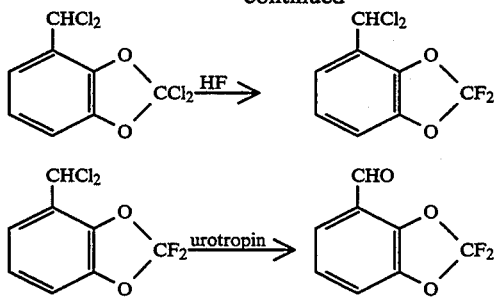

The benzo[1,3]-dioxole-carbaldehydes of the formula (II) required as starting substances for the preparation of the process according to the invention are known (compare Tetrahedron Letters No. 38, 3361-3364 (1976)) and can be prepared by analogous processes.

The chlorinating agents furthermore to be used in the 1st stage, the hydrogen fluoride in the 2nd stage and the urotropin in the 3rd stage are common and commercially available chemicals.

The 2,2-dichlorodichloromethyl-benzo(1,3)-dioxoles of the formula (III) which occur as intermediate products and the 2,2-difluoro-dichloromethyl-benzo(1,3)-dioxoles of the formula (IV) are new and likewise form part of the invention.

Chlorinating agents are required in stage 1. All the customary chlorinating agents, such as, for example, phosphorus chlorides, such as phosphorus pentachloride, or phosphorus chlorides and chlorine, such as, for example, phosphorus trichloride or phosphorus pentachloride and chlorine, can be used.

If chlorine is used, free radical initiators, such as, for example, AIBN, or azo-bis-isobutyronitrile, are added in equivalent amounts of 0.001-0.05. The reaction can also be carried out in the presence of high-energy light, such as UV light. The 1st stage is preferably carried out without a solvent. However, chlorinated hydrocarbons, such as, for example, perchlorinated hydrocarbons, such as carbon tetrachloride, are also suitable.

The temperatures can be varied within a substantial range. The reaction is in general carried out at temperatures between 0° C. and 220° C., preferably at temperatures between 80° C. and 180° C., particularly preferably at temperatures between 100° C. and 160° C.

The ratio of chlorinating agent employed, such as phosphorus pentachloride, to starting material of the formula (II) is preferably 2:1 to 4:1, preferably 2.1:1.

Hydrogen fluoride is employed as the fluorinating agent in stage 2.

If appropriate, stage 2 can be carried out in the presence of a solvent or diluent. Possible solvents or diluents are alkylated aromatics, such as toluene, and chlorinated aromatics, such as chlorobenzene. The reaction is preferably carried out without a solvent.

The ratio of hydrogen fluoride to starting substance of the formula (III) in stage 2 is between 2:1 and 20:1, preferably between 5:1 and 15:1 and particularly preferably between 7:1 and 10:1.

The reaction temperature can be varied within a substantial range in stage 2. The reaction is in general carried out at temperatures between $-30°$ C. and $+80°$ C., preferably between $-20°$ C. and $+40°$ C. and particularly preferably between $-10°$ C. and $+10°$ C.

The sequence of the addition is not of particular importance. However, addiction of hydrogen fluoride to the compounds of the formula III at temperatures $>0°$ C. is preferred, depending on the reaction temperature.

Stage 3 is carried out in aqueous solution.

The reaction temperature can be varied within a substantial range in stage 3. The reaction is in general carried out between 20° C. and 150° C., preferably between 60° C. and 120° C. and particularly preferably between 80° C. and 110° C.

The ratio of urotropin to the starting material of the formula (IV) in stage 3 is between 2:1 and 1:1, preferably 1:1.

In the 1st stage, the end of the evolution of hydrogen chloride is awaited, the solvent, if used, is then distilled off, and if phosphorus pentachloride is used, the phosphorus oxychloride and phosphorus(III) chloride are distilled off, and the product is distilled in vacuo.

The end of the evolution of hydrogen chloride is also awaited in the 2nd stage, which takes, for example, about 3 hours at $-10°$ C. The excess hydrogen fluoride is distilled off, or is separated off as its own phase. Residues of hydrogen fluoride can be neutralised, for example, with CaO, NaF or KF, or washed out with water.

The 3rd stage is subjected to aqueous extraction after about 16 hours and is then distilled.

The 2,2-difluorobenzo (1,3)dioxole-carbaldehydes obtainable with the aid of the process according to the invention can be employed as starting compounds for highly active medicaments, for example for combating circulatory diseases (compare DE 3 716 652).

The 2,2-difluorobenzo(1,3)-dioxole-carbaldehydes can of course also be used as starting compounds for other highly active compounds in the pharmaceuticals sector and, for example, in the plant protection sector.

PREPARATION EXAMPLES

Example 1

Stage 1.1

4-Dichloromethyl-2,2-dichlorobenzo[1,3]dioxole

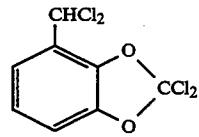

150.0 g (1.0 mol) of 2,3-methylenedioxybenzaldehyde are added in portions to 625.0 g (3.0 mol) of phosphorus pentachloride under nitrogen. The mixture is heated and stirred at 140° C. for 5 hours (until the HCl evolution has ended). The phosphorus oxychloride formed and phosphorus(III) chloride are then distilled off and the product is distilled in vacuo. 260.0 g (95% of theory) of 4-dichloromethyl-2,2-dichlorobenzo[1,3]dioxole of boiling point 142° C./16 mbar are isolated.

Stage 1.2

4-Dichloromethyl-2,2-difluorobenzo[1,3]dioxole

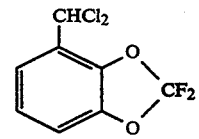

80.0 g (4.0 mol) of anhydrous hydrogen fluoride are metered into 110.0 g (0.4 mol) of 4-dichloromethyl-2,2- dichlorobenzo[1,3]dioxole at −10° C. The mixture is then stirred vigorously at −10° C. for a further 2 hours. Most of the hydrogen fluoride is stripped off in a vacuum of down to 50 mbar at −10° C. After separation of the phases, the organic phase is shaken with ice-water, separated off, dried and distilled. 77 g (80% of theory) of 4-dichloromethyl-2,2-difluoro-benzo[1,3]dioxole of boiling point 90°–92° C./16 mbar are obtained.

Stage 1.3

2,2-Difluorobenzo[1,3]dioxole-4-carbaldehyde

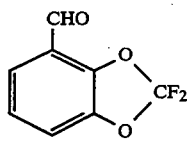

48.0 g (0.2 mol) of 4-dichloromethyl-2,2-difluorobenzo[1,3]dioxole are stirred under reflux with 28.0 g (0.2 mol) of urotropin (hexamethylenetetramine, formin) in 200 ml of 50% strength acetic acid for 16 hours. 80 ml of concentrated hydrochloric acid are then added and the mixture is stirred under reflux for a further hour. After cooling, the mixture is poured onto 200 g of ice and extracted three times with 300 ml of methyl tertbutyl ether each time, the extracts are washed with 300 ml of sodium bicarbonate solution and water, dried over magnesium sulphate and concentrated and the residue is distilled. 32 g (86% of theory) of 2,2-difluorobenzo[1,3-]dioxole-4-carbaldehyde of boiling point 105°–106° C./50 mbar are isolated.

Example 2

Stage 2.1

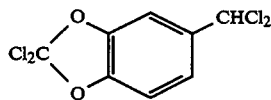

700 g (3.36 mol) of phosphorus pentachloride are initially introduced into a stirred apparatus and 150 g (1.0 mol) of methylenedioxybenzaldehyde are added dropwise. Thorough mixing is ensured here by very slow movement of the stirrer. Towards the end of the dropwise addition, the reaction mixture becomes stirrable in a normal manner and is then heated at 120° C. The evolution of hydrogen chloride lasts about 5 hours at 120° C. The phosphorus oxychloride formed is then distilled off and the product is subsequently distilled in vacuo. 238 g (82.6% of theory) of 5-dichloromethyl-2,2-dichlorobenzodioxole of boiling point 108°–10° C./0.04 mbar are obtained.

Stage 2.2

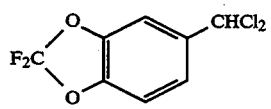

50 ml of hydrogen fluoride are initially introduced into a fluorination apparatus of V4A steel at −15° C. and a mixture of 130 g (0.45 mol) of 5-dichloromethyl-2,2-dichloro-benzodioxole and 100 ml of dry chlorobenzene is added dropwise, with exclusion of moisture. The mixture is then stirred at −10° C. for 4 hours, warmed to 0° C. and subsequently stirred until the evolution of hydrogen chloride has ended (about 2 hours). After separation of the phases, the organic phase is shaken with ice-water, separated off, dried over sodium sulphate and distilled.

79 g (73% of theory) of 5-dichloromethyl-2,2-difluorobenzo-(1,3)-dioxole of boiling point 98°–100° C./10 mbar are obtained.

Stage 2.3

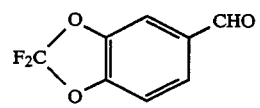

A mixture of 80 g (0.57 mol) of urotropin, 150 ml of water and 80 g (0.33 mol) of 5-dichloromethyl-2,2-difluorobenzo-(1,3)-dioxole is stirred at 100° C. for 2 hours, 100 ml of water and 50 ml of concentrated hydrochloric acid are then added and the mixture is stirred again at 100° C. for 2 hours. Steam distillation gives, after separation of the phases, 58 g (94% of theory) of 2,2-difluorobenzodioxole-5-carbaldehyde (purity ~99%) having a refractive index $n_D^{20}$ of 1.4982.

Precursors

Example a

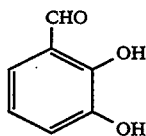

152.0 g (1.0 mol) of o-vanillin and 200 ml of azeotropic hydrobromic acid (47.5% strength) are stirred under reflux in 500 ml of glacial acetic acid for 2.5 hours. The acid mixture is then distilled off and the residue is subjected to fractional vacuum distillation. The redistilled fraction having a boiling point of 120°–125° C./12 mbar is purified by recrystallisation from 1 l of heptane (hexane is also possible and is recovered). 97 g (70% of theory) of 2,3-dihydroxybenzaldehyde of melting point 105°–107° C. are obtained.

Example b

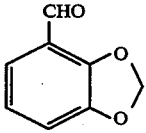

138.0 g (1.0 mol) of 2,3-dihydroxybenzaldehyde, 415.0 g (3.0 mol) of potassium carbonate, 4.7 g of copper oxide, 255.0 g (3.0 mol) of methylene chloride and 1500 ml of distilled dimethylformamide are boiled for 7 hours, while stirring intensively.. The reaction mixture is evaporated to dryness in vacuo and, after addition of 1000 ml of ice-water to the residue, the mixture is extracted four times by shaking with 300 ml of methyl tert-butyl ether each time. The combined ether extracts are washed with 5% strength sodium hydroxide solution and water and dried over sodium sulphate. The methyl tert-butyl ether is then stripped off (and can be reused) and the residue is distilled in vacuo at 92°–93° C./1 mbar. 120 g (80% of theory) of 2,3-methylenedioxybenzaldehyde having a melting point of 32°–33° C. are obtained.

We claim:

1. A process for the preparation of a 2,2-difluorobenzo(1,3)-dioxole-carbaldehyde of the formula

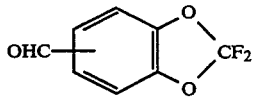
(I)

which comprises reacting a benzo(1,3)-dioxole-carbaldehyde of the formula

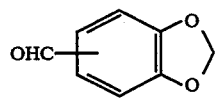
(II)

with chlorinating agents, in a first stage to produce a chlorine-substituted benzo(1,3)-dioxole of the formula

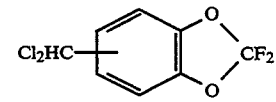
(III)

partially fluorinating said chlorine-substituted benzo(1,3)-dioxole by means of hydrogen fluoride to produce a compound of the formula

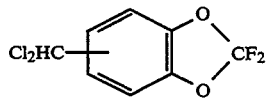
(IV)

and reacting the Compound (IV) with urotropin to produce the Compound (I).

2. A process according to claim 1, wherein the partial fluorination is carried out at a temperature from −30° C. to +80° C., and the reaction with urotropin is carried out at a temperature from 20° C. to 150° C.

3. A process according to claim 1, wherein the partial fluorination is carried out at a temperature from −20° C. to +40° C., and the reaction with urotropin is carried out at a temperature from 60° C. to 120° C.

* * * * *